United States Patent
Weingarten et al.

(10) Patent No.: US 12,059,281 B2
(45) Date of Patent: Aug. 13, 2024

(54) SYSTEMS AND METHODS OF FLUORO-CT IMAGING FOR INITIAL REGISTRATION

(71) Applicant: Covidien LP, Mansfield, MA (US)

(72) Inventors: Oren P. Weingarten, Herzliya (IL); Guy Alexandroni, Ramat Hasharon (IL); Evgeni Kopel, Herzliya (IL)

(73) Assignee: Covidien LP, Mansfield, MA (US)

( * ) Notice: Subject to any disclaimer, the term of this patent is extended or adjusted under 35 U.S.C. 154(b) by 254 days.

(21) Appl. No.: 16/889,431

(22) Filed: Jun. 1, 2020

(65) Prior Publication Data
US 2021/0052240 A1 Feb. 25, 2021

Related U.S. Application Data

(60) Provisional application No. 62/888,905, filed on Aug. 19, 2019.

(51) Int. Cl.
| | |
|---|---|
| *A61B 6/00* | (2024.01) |
| *A61B 6/46* | (2024.01) |
| *A61B 34/10* | (2016.01) |
| *G06T 7/32* | (2017.01) |

(52) U.S. Cl.
CPC .............. *A61B 6/487* (2013.01); *A61B 6/466* (2013.01); *A61B 6/488* (2013.01); *A61B 34/10* (2016.02); *G06T 7/32* (2017.01); *A61B 2034/102* (2016.02); *A61B 2034/107* (2016.02)

(58) Field of Classification Search
CPC . G06T 2207/10064; G06T 2207/10081; G06T 2207/10072; G06T 2207/10068; G06T 2207/30021; G06T 2207/30061; G06T 7/32; G06T 7/33; A61B 2034/102; A61B 2034/107; A61B 34/10; A61B 6/466; A61B 6/487; A61B 6/488

See application file for complete search history.

(56) References Cited

U.S. PATENT DOCUMENTS

| | | |
|---|---|---|
| 6,373,916 B1 | 4/2002 | Inoue et al. |
| 6,473,634 B1 | 10/2002 | Barni |
| 7,551,759 B2 | 6/2009 | Hristov et al. |
| 7,916,918 B2 | 3/2011 | Suri et al. |
| 8,335,359 B2 | 12/2012 | Fidrich et al. |
| 8,482,606 B2 | 7/2013 | Razzaque et al. |
| 8,625,869 B2 | 1/2014 | Harder et al. |
| 8,706,184 B2 | 4/2014 | Mohr et al. |

(Continued)

FOREIGN PATENT DOCUMENTS

| | | |
|---|---|---|
| BR | 0013237 A | 7/2003 |
| BR | 0116004 A | 6/2004 |

(Continued)

OTHER PUBLICATIONS

Extended European Search Report issued in European Application No. 20191081.7 dated Apr. 14, 2021.

(Continued)

*Primary Examiner* — Sing-Wai Wu
(74) *Attorney, Agent, or Firm* — Weber Rosselli & Cannon LLP

(57) ABSTRACT

A system and method for registration of a pre-procedural image data set (e.g. CT data) or a 3D model derived therefrom with a patient's luminal structure (e.g., airways in the lungs) using intraprocedural fluoroscopic imaging techniques.

15 Claims, 10 Drawing Sheets

(56) References Cited

U.S. PATENT DOCUMENTS

| | | |
|---|---|---|
| 8,827,934 B2 | 9/2014 | Chopra et al. |
| 9,433,390 B2 | 9/2016 | Nathaniel et al. |
| 9,710,921 B2 | 7/2017 | Wong et al. |
| 9,833,167 B2 | 12/2017 | Cohen et al. |
| 9,888,898 B2 | 2/2018 | Imagawa et al. |
| 9,918,659 B2 | 3/2018 | Chopra et al. |
| 10,127,629 B2 | 11/2018 | Razzaque et al. |
| 10,130,316 B2 | 11/2018 | Funabasama et al. |
| 10,373,719 B2 | 8/2019 | Soper et al. |
| 10,376,178 B2 | 8/2019 | Chopra |
| 10,405,753 B2 | 9/2019 | Sorger |
| 10,478,162 B2 | 11/2019 | Barbagli et al. |
| 10,480,926 B2 | 11/2019 | Froggatt et al. |
| 10,524,866 B2 | 1/2020 | Srinivasan et al. |
| 10,555,788 B2 | 2/2020 | Panescu et al. |
| 10,610,306 B2 | 4/2020 | Chopra |
| 10,638,953 B2 | 5/2020 | Duindam et al. |
| 10,674,970 B2 | 6/2020 | Averbuch et al. |
| 10,682,070 B2 | 6/2020 | Duindam |
| 10,706,543 B2 | 7/2020 | Donhowe et al. |
| 10,709,506 B2 | 7/2020 | Coste-Maniere et al. |
| 10,772,485 B2 | 9/2020 | Schlesinger et al. |
| 10,796,432 B2 | 10/2020 | Mintz et al. |
| 10,823,627 B2 | 11/2020 | Sanborn et al. |
| 10,827,913 B2 | 11/2020 | Ummalaneni et al. |
| 10,835,153 B2 | 11/2020 | Rafii-Tari et al. |
| 10,885,630 B2 | 1/2021 | Li et al. |
| 10,896,506 B2 | 1/2021 | Zhao et al. |
| 2003/0013972 A1 | 1/2003 | Makin |
| 2012/0059248 A1* | 3/2012 | Holsing ............. A61B 5/062 600/424 |
| 2013/0303945 A1 | 11/2013 | Blumenkranz et al. |
| 2014/0035798 A1 | 2/2014 | Kawada et al. |
| 2014/0229881 A1* | 8/2014 | Schadewaldt ....... G06F 3/04855 715/771 |
| 2015/0148690 A1 | 5/2015 | Chopra et al. |
| 2015/0265368 A1 | 9/2015 | Chopra et al. |
| 2016/0005224 A1 | 1/2016 | Greenburg |
| 2016/0157939 A1 | 6/2016 | Larkin et al. |
| 2016/0183841 A1 | 6/2016 | Duindam et al. |
| 2016/0192860 A1 | 7/2016 | Allenby et al. |
| 2016/0242724 A1* | 8/2016 | Lavallee ............. A61B 6/584 |
| 2016/0287344 A1 | 10/2016 | Donhowe et al. |
| 2017/0035380 A1 | 2/2017 | Barak et al. |
| 2017/0112576 A1 | 4/2017 | Coste-Maniere et al. |
| 2017/0209071 A1 | 7/2017 | Zhao et al. |
| 2017/0265952 A1 | 9/2017 | Donhowe et al. |
| 2017/0311844 A1 | 11/2017 | Zhao et al. |
| 2017/0319165 A1 | 11/2017 | Averbuch |
| 2018/0078318 A1 | 3/2018 | Barbagli et al. |
| 2018/0153621 A1 | 6/2018 | Duindam et al. |
| 2018/0235709 A1 | 8/2018 | Donhowe et al. |
| 2018/0240237 A1 | 8/2018 | Donhowe et al. |
| 2018/0256262 A1 | 9/2018 | Duindam et al. |
| 2018/0263706 A1 | 9/2018 | Averbuch |
| 2018/0279852 A1 | 10/2018 | Rafii-Tari et al. |
| 2018/0325419 A1 | 11/2018 | Zhao et al. |
| 2019/0000559 A1 | 1/2019 | Berman et al. |
| 2019/0000560 A1 | 1/2019 | Berman et al. |
| 2019/0008413 A1 | 1/2019 | Duindam et al. |
| 2019/0038365 A1 | 2/2019 | Soper et al. |
| 2019/0065209 A1 | 2/2019 | Mishra et al. |
| 2019/0110839 A1 | 4/2019 | Rafii-Tari et al. |
| 2019/0175062 A1 | 6/2019 | Rafii-Tari et al. |
| 2019/0183318 A1 | 6/2019 | Froggatt et al. |
| 2019/0183585 A1 | 6/2019 | Rafii-Tari et al. |
| 2019/0183587 A1 | 6/2019 | Rafii-Tari et al. |
| 2019/0192234 A1 | 6/2019 | Gadda et al. |
| 2019/0209016 A1 | 7/2019 | Herzlinger et al. |
| 2019/0209043 A1 | 7/2019 | Zhao et al. |
| 2019/0216548 A1 | 7/2019 | Ummalaneni |
| 2019/0239723 A1 | 8/2019 | Duindam et al. |
| 2019/0239831 A1 | 8/2019 | Chopra |
| 2019/0250050 A1 | 8/2019 | Sanborn et al. |
| 2019/0254649 A1 | 8/2019 | Walters et al. |
| 2019/0269470 A1 | 9/2019 | Barbagli et al. |
| 2019/0272634 A1 | 9/2019 | Li et al. |
| 2019/0298160 A1 | 10/2019 | Ummalaneni et al. |
| 2019/0298451 A1 | 10/2019 | Wong et al. |
| 2019/0320878 A1 | 10/2019 | Duindam et al. |
| 2019/0320937 A1 | 10/2019 | Duindam et al. |
| 2019/0336238 A1 | 11/2019 | Yu et al. |
| 2019/0343424 A1 | 11/2019 | Blumenkranz et al. |
| 2019/0350659 A1 | 11/2019 | Wang et al. |
| 2019/0365199 A1 | 12/2019 | Zhao et al. |
| 2019/0365479 A1 | 12/2019 | Rafii-Tari |
| 2019/0365486 A1 | 12/2019 | Srinivasan et al. |
| 2019/0380787 A1 | 12/2019 | Ye et al. |
| 2020/0000319 A1 | 1/2020 | Saadat et al. |
| 2020/0000526 A1 | 1/2020 | Zhao |
| 2020/0008655 A1 | 1/2020 | Schlesinger et al. |
| 2020/0030044 A1 | 1/2020 | Wang et al. |
| 2020/0030461 A1 | 1/2020 | Sorger |
| 2020/0038750 A1 | 2/2020 | Kojima |
| 2020/0043207 A1 | 2/2020 | Lo et al. |
| 2020/0046431 A1 | 2/2020 | Soper et al. |
| 2020/0046436 A1 | 2/2020 | Tzeisler et al. |
| 2020/0054399 A1 | 2/2020 | Duindam et al. |
| 2020/0060771 A1 | 2/2020 | Lo et al. |
| 2020/0069192 A1 | 3/2020 | Sanborn et al. |
| 2020/0077870 A1 | 3/2020 | Dicarlo et al. |
| 2020/0078095 A1 | 3/2020 | Chopra et al. |
| 2020/0078103 A1 | 3/2020 | Duindam et al. |
| 2020/0085514 A1 | 3/2020 | Blumenkranz |
| 2020/0109124 A1 | 4/2020 | Pomper et al. |
| 2020/0129045 A1 | 4/2020 | Prisco |
| 2020/0129239 A1 | 4/2020 | Bianchi et al. |
| 2020/0138515 A1 | 5/2020 | Wong |
| 2020/0155116 A1 | 5/2020 | Donhowe et al. |
| 2020/0170623 A1 | 6/2020 | Averbuch |
| 2020/0170720 A1 | 6/2020 | Ummalaneni |
| 2020/0179058 A1 | 6/2020 | Barbagli et al. |
| 2020/0188038 A1 | 6/2020 | Donhowe et al. |
| 2020/0205903 A1 | 7/2020 | Srinivasan et al. |
| 2020/0205904 A1 | 7/2020 | Chopra |
| 2020/0214664 A1 | 7/2020 | Zhao et al. |
| 2020/0229679 A1 | 7/2020 | Zhao et al. |
| 2020/0242767 A1 | 7/2020 | Zhao et al. |
| 2020/0275860 A1 | 9/2020 | Duindam |
| 2020/0297442 A1 | 9/2020 | Adebar et al. |
| 2020/0315554 A1 | 10/2020 | Averbuch et al. |
| 2020/0330795 A1 | 10/2020 | Sawant et al. |
| 2020/0352427 A1 | 11/2020 | Deyanov |
| 2020/0364865 A1 | 11/2020 | Donhowe et al. |

FOREIGN PATENT DOCUMENTS

| | | |
|---|---|---|
| CZ | 486540 | 9/2016 |
| CZ | 2709512 | 8/2017 |
| CZ | 2884879 | 1/2020 |
| EP | 3413830 A4 | 9/2019 |
| EP | 3478161 A4 | 2/2020 |
| EP | 3641686 A2 | 4/2020 |
| EP | 3644885 A1 | 5/2020 |
| EP | 3644886 A1 | 5/2020 |
| MX | PA03005028 A | 1/2004 |
| MX | 225663 B | 1/2005 |
| MX | 226292 | 2/2005 |
| MX | 246862 B | 6/2007 |
| MX | 265247 | 3/2009 |
| MX | 284569 B | 3/2011 |
| WO | 2017030915 A1 | 2/2017 |
| WO | 2017139621 A1 | 8/2017 |

OTHER PUBLICATIONS

Partial European Search Report issued in European Patent Application No. 20191081.7 dated Dec. 11, 2020.

Communication pursuant to Article 94(3) EPC issued in European Patent Application No. 20191081.7 dated May 8, 2023.

* cited by examiner

SYSTEMS AND METHODS OF FLUORO-CT IMAGING FOR INITIAL REGISTRATION

CROSS-REFERENCE TO RELATED APPLICATION

The present application claims the benefit of and priority to U.S. Provisional Patent Application Ser. No. 62/888,905, filed on Aug. 19, 2019, the entire content of which is incorporated herein by reference.

FIELD

The disclosure relates to surgical imaging systems, and more particularly, to systems and methods for assisting a clinician performing surgery by registering pre-procedure images with intra-procedure images for navigation of tools through luminal networks.

BACKGROUND

There exist several commonly applied medical methods, such as endoscopic procedures or minimally invasive procedures, for treating various maladies affecting organs including the liver, brain, heart, lung, gall bladder, kidney and bones. Often, one or more imaging modalities, such as magnetic resonance imaging (MRI), ultrasound imaging, computed tomography (CT), fluoroscopy as well as others are employed by clinicians to identify and navigate to areas of interest within a patient and ultimately a target for treatment.

For example, an endoscopic approach has proven useful in navigating to areas of interest within a patient, and particularly so for areas within luminal networks of the body such as the lungs. To enable the endoscopic approach, and more particularly the bronchoscopic approach in the lungs, endobronchial navigation systems have been developed that use pre-procedural or previously acquired MRI data or CT image data to generate a three-dimensional (3D) renderings or models of the particular body part. The resulting 3D model or rendering generated from the MRI scan or CT scan is then utilized to create a navigation plan to facilitate the advancement of a navigation catheter (or other suitable medical device) through the bronchoscope and the luminal network, for example airways of a patient's lungs to an identified target or area of interest.

However, to be of use in navigation to a target or area of interest within the patient's lungs the 3D model or rendering of the lungs derived from the pre-procedural images must be registered to the patient's lungs. That is in order to ensure that the bronchoscope and other tools being inserted into the patient are following the pre-procedural plan, the position of the bronchoscope and other tools within the patient must be aligned with the pre-procedure plan.

While current registration techniques are effective, improvements are always desired, particularly improvements that can reduce the clinical hardware needed to perform the registration.

SUMMARY

The disclosure is systems and method of registering fluoroscopic images and tissues and medical device found therein to pre-procedure CT image data. Further, the disclosure is directed to systems and methods of registering sensor location and position data to fluoroscopic images. Still further the disclosure is directed to using fluoroscopic imaging to register sensor location and position data with pre-operative CT image data.

One aspect of the disclosure is a method of registering two image data sets, including performing a fluoroscopic sweep of a desired portion of a patient and generating a 3D reconstruction from data received from the fluoroscopic sweep. The method also includes receiving an indication of a point in the 3D reconstruction that appears in a pre-procedure CT image data, registering the 3D reconstruction to the pre-procedure CT image data, displaying the 3D reconstruction, and displaying portions of a navigation plan associated with the pre-procedure CT image data on the 3D reconstruction. Other embodiments of this aspect include corresponding computer systems, apparatus, and computer programs recorded on one or more computer storage devices, each configured to perform the actions of the methods.

Implementations may include one or more of the following features. The received indication of a point may be the position of a main carina in the 3D reconstruction. The method may further include a step of receiving an indication of two additional points in the 3D reconstruction. The indications of the indicated three points may be matched to points in the pre-procedure CT image data. The method may further include solving for two additional angles of orientation of the 3D reconstruction such that the 3D reconstruction matches the pre-procedure CT image data. The method where the 3D reconstruction matches a 3D model derived from the pre-procedure CT image data. The method may further include conducting a search of the 3D reconstruction and the pre-procedure CT image data to identify points of correlation. The method may further include a step of receiving an indication of a point in the 3D reconstruction that appears in a pre-procedure CT image data is a confirmation of a point selected from the search. The method may further include solving for three orientation angles such that the orientation of the 3D reconstruction matches the pre-procedure CT image data. The displaying portions of a navigation plan depicts the position of a target identified in the pre-procedure CT image data on the 3D reconstruction. The displaying portions of a navigation plan depicts a pathway through a luminal network to the target. Implementations of the described techniques may include hardware, a method or process, or computer software on a computer-accessible medium.

One general aspect includes a system for registering fluoroscopic image data with pre-operative CT image data including: a computing device including a processor and a memory, the memory storing therein an application that when executed by the processor causes the processor to execute the steps of generating a 3D reconstruction from data received from the fluoroscopic sweep, receiving an indication of a point in the 3D reconstruction that appears in a pre-procedure CT image data, registering the 3D reconstruction to the pre-procedure CT image data, and displaying the 3D reconstruction. The system further includes a display for displaying a portion of a navigation plan associated with the pre-procedure CT image data on the 3D reconstruction based on the registration.

A further aspect is directed to a method for registering an image to a patient including receiving location data of a sensor associated with the catheter, performing a fluoroscopic sweep. The method also includes generating a 3D reconstruction from data received from the fluoroscopic sweep and generating 2D slice images from the 3D reconstruction. The method also includes receiving an indication of the location of the catheter in the 2D slice images and registering the 3D reconstruction to the location data of the sensor.

The method may further include receiving a second indication of the location of the catheter in a second 2D slice image. Additionally, the method may include performing image processing to determine the location of the catheter in additional 2D slice images. The indication of the location of the catheter in the 2D slice images may be generated by image processing techniques. The method may further include receiving an indication of a point in the 3D reconstruction that appears in a pre-procedure CT image data, registering the 3D reconstruction to the pre-procedure CT image data, displaying the 3D reconstruction, and displaying portions of a navigation plan associated with the pre-procedure CT image data on the 3D reconstruction. The method may further include displaying a position of the sensor associated with the catheter in the 3D reconstruction based on the received location data. The method further including updating the position of the sensor associated with the catheter as the catheter is navigated through a luminal network and new location data is received.

BRIEF DESCRIPTION OF THE DRAWINGS

Various aspects and features of the disclosure are described hereinbelow with references to the drawings, wherein.

DETAILED DESCRIPTION

The disclosure is directed to a system and method that enables registration of a pre-procedural image data set (e.g. CT data) or a 3D model derived therefrom with a patient's luminal structure (e.g., airways in the lungs) using intraprocedural fluoroscopic imaging techniques.

Registration can be performed using a variety of techniques. For example, robotic systems can be deployed to navigate an endoscope to points within the lung. By contacting these points with the endoscope and correlating their position within the patient's lungs with positions within the 3D model the 3D model is registered to the patient's lungs, and with the coordinate system of the robot. In this manner the robot can then determine where within the lungs of the patient the area of interest is located and follow the navigation plan to the area of interest or develop a pathway through the lungs to the area of interest.

Similarly, flexible sensors may be employed to achieve registration. As the robot or a clinician navigates an endoscope within the patient, the shape of the flexible sensors (formed on or in the endoscope or other tools) as they advance and bend through the airways can have their sensed shape matched to the airways in the 3D model or rendering. This shape matching results in registration of the position of the endoscope in the patient to a position in a luminal network within the 3D model that has the same shape.

Yet a further method of registration employs electromagnetic (EM) sensors and EM navigation. The endoscope or another tool may include an EM sensor. An EM field generator generates an EM field, and when the EM sensor is placed in the EM field, a current is produced. That current is fed to a computer which can determine X, Y, Z, pitch, yaw, and roll coordinates (six degrees of freedom) of the EM sensor within the magnetic field. In practice registration can be performed in at least two different ways. In one, similar to the robotic system described above, the EM sensor can be placed in pre-defined locations within the patient that can be observed with a bronchoscope. Usually this is between 4 and 10 points. The matching of these points to the same points in the 3D model or rendering, results in a registration of the 3D model with the patient. In a second method, the coordinates of the EM sensor are collected as the EM sensor is navigated through the luminal network. As many hundreds or thousands of these coordinates are collected a point cloud of coordinates is created. The point cloud, which are assumed to be taken from within the luminal network has a 3D dimensional shape that can then be matched to the 3D shape of the interior of the luminal network. Once matched the luminal network in the 3D model and the luminal network of the patient are registered. Once registered the detected position of the EM sensor can be used to follow a navigation plan in the 3D model to an area of interest within the luminal network of the patient.

Figure 1:
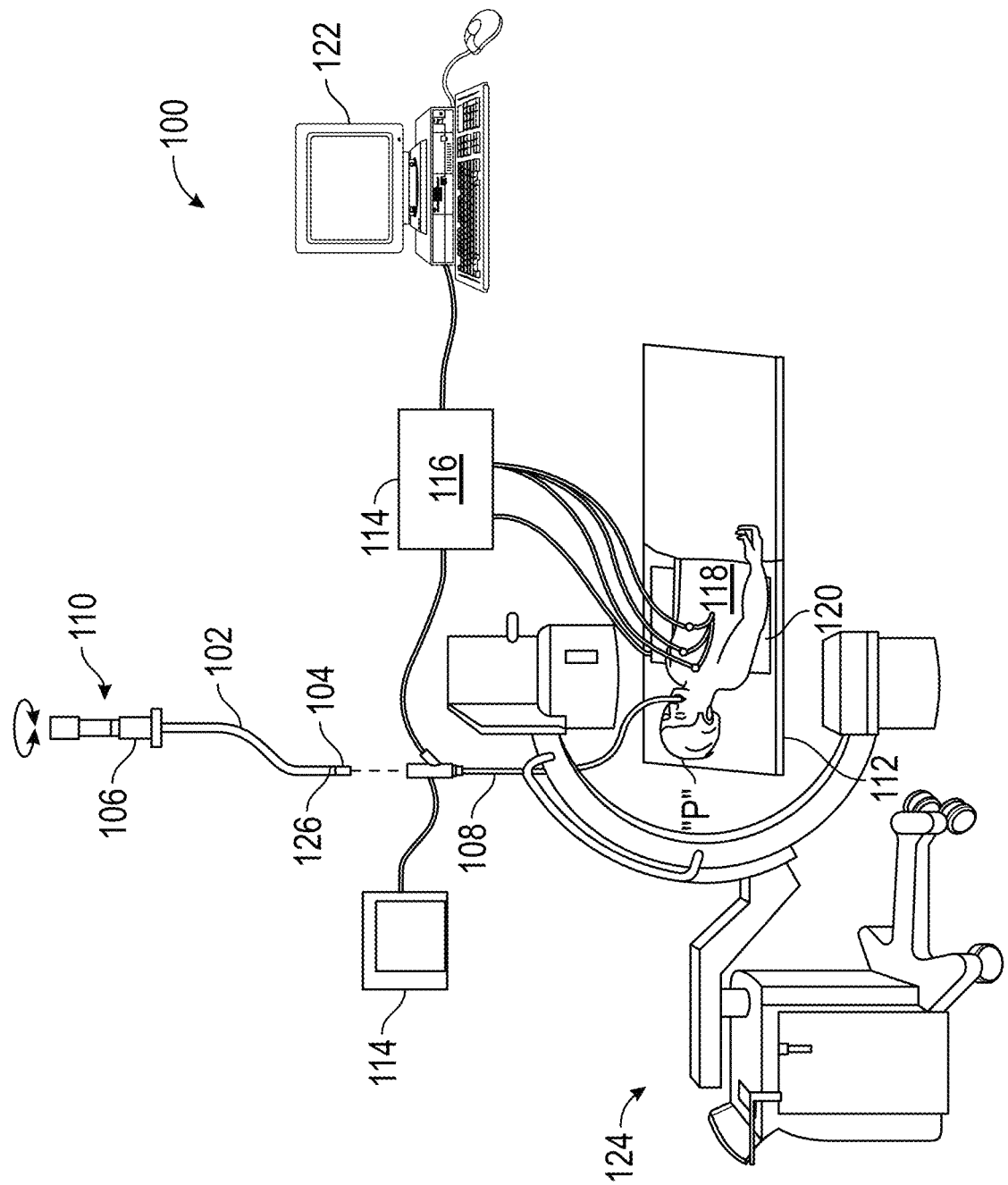
FIG. 1 depicts an imaging and navigation system in accordance with the disclosure.

FIG. 1 is a perspective view of an exemplary system for navigation of a medical device, e.g., a biopsy or treatment tool, to a target via airways of the lungs. One aspect of the system 100 is a software application for reviewing computed tomography (CT) image data that has been acquired separately from system 100. The review of the CT image data allows a user to identify one or more targets and plan a pathway to an identified target. This is typically referred to as a planning phase. Another aspect of the software application is a navigation phase which allows a user to navigate a catheter or other tool to a target (navigation phase) using a user interface and confirm placement of the catheter or a tool relative to the target. The target is typically tissue of interest for biopsy or treatment that was identified during the planning phase by review of the CT image data. Following navigation, a medical device, such as a biopsy tool or treatment tool, may be inserted into the catheter to obtain a tissue sample from the tissue located at, or proximate to, the target or to treat such tissue. The treatment tool may be selected to achieve microwave ablation, radio-frequency ablation, cryogenic ablation, chemical ablation, or other treatment mechanism of the target as preferred by the clinician.

One aspect of FIG. 1 is a catheter system 102 including a sensor 104 at a distal end. The catheter system 102 includes a catheter 106. In practice, catheter 106 is inserted into a bronchoscope 108 for access to a luminal network of the patient P. Specifically, catheter 106 of catheter guide assembly 106 may be inserted into a working channel of bronchoscope 108 for navigation through a patient's luminal network. If configured for EMN (as described below), a locatable guide (LG) 110, which may include the sensor 104 such as an EM sensor may be inserted into catheter 106 and locked into position such that sensor 104 extends a desired distance beyond the distal tip of catheter 106. However, it should be noted that the sensor 104 may be incorporated into one or more of the bronchoscope 108, catheter 106, or a biopsy or treatment tool, without departing from the scope of the disclosure.

If the catheter 106 is inserted into the bronchoscope 108, the distal end of the EWC 102 and LG 110 both extend beyond the distal end of the bronchoscope 108. The position or location and orientation of sensor 104 and thus the distal portion of LG 110, within an electromagnetic field can be derived based on location data in the form of currents produced by the presence of the EM sensors in a magnetic field, or by other means described herein. Though the use of EM sensors and EMN are not required as part of this disclosure, their use may further augment the utility of the disclosure in endoluminal navigation (e.g., navigation of the lungs). As the bronchoscope 108, catheter 106, LG 110 or other tool could be used interchangeably or in combination herein, the term catheter will be used here to refer to one or more of these elements. Further, as an alternative to the use of EM sensors, flex sensors such as fiber Bragg sensors, ultrasound sensors, accelerometers, and others may be used in conjunction with the present disclosure to provide outputs to the tracking system 114 for determination of the position of a catheter including without limitation the bronchoscope 108, catheter 106, LG 110, or biopsy or treatment tools, without departing from the scope of the present disclosure.

Figure 7:
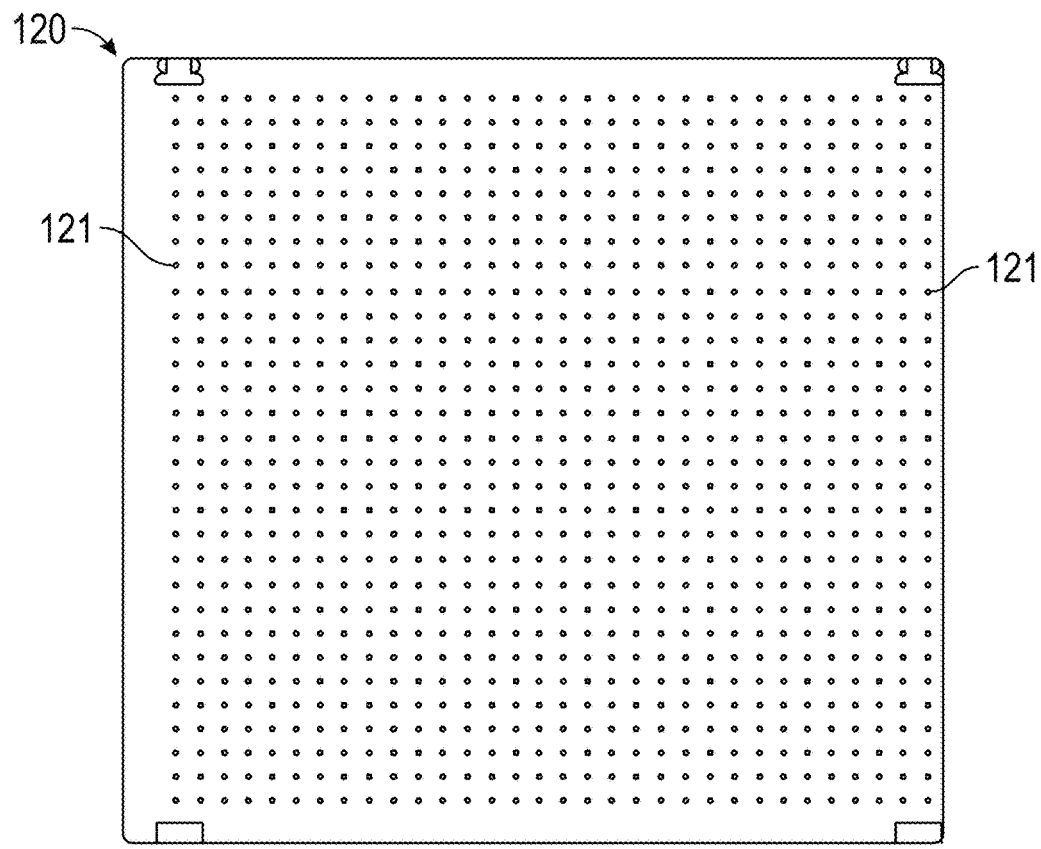
FIG. 7 depicts a matt with markers to be placed under a patient in accordance with the disclosure.

System 100 generally includes an operating table 112 configured to support a patient P, a bronchoscope 108 configured for insertion through patient P's mouth into patient P's airways; monitoring equipment 114 coupled to bronchoscope 108 (e.g., a video display, for displaying the video images received from the video imaging system of bronchoscope 108). If configured for EMN, system 100 may include a locating or tracking system 114 and a locating module 116, a plurality of reference EM sensors 118 and a transmitter mat 120 including a plurality of incorporated markers (FIG. 7). Though shown in FIG. 7 as a repeating pattern of markers, other patterns, including three dimensional markers are different relative depths in the transmitter mat 120, or a non-repeating pattern may be employed without departing from the scope of the present disclosure. Also included is a computing device 122 including software and/or hardware used to facilitate identification of a target, pathway planning to the target, navigation of a medical device to the target, and/or confirmation and/or determination of placement of catheter 106, or a suitable device therethrough, relative to the target. Computing device 122 may be similar to workstation 1001 of FIG. 8 and may be configured to execute the methods of the disclosure including the methods of FIGS. 2 and 3, Computing device 122 may be any suitable computing device including a processor and storage medium, wherein the processor is capable of executing instructions stored on the storage medium as one or more applications. Computing device 122 may further include a database configured to store patient data, CT data sets including CT images, fluoroscopic data sets including fluoroscopic images and video, fluoroscopic 3D reconstruction, navigation plans, and any other such data. Although not explicitly illustrated, computing device 122 may include inputs, or may otherwise be configured to receive, CT data sets, fluoroscopic images/ video and other data described herein. Additionally, computing device 122 includes a display configured to display graphical user interfaces. Computing device 122 may be connected to one or more networks through which one or more databases may be accessed. Further details of the computing device are described in connection with FIG. 8, below.

With respect to the planning phase, computing device 122 utilizes previously acquired CT image data for generating and viewing a three-dimensional model or rendering of patient P's airways, enables the identification of a target on the three-dimensional model (automatically, semi-automatically, or manually), and allows for determining a pathway through patient P's airways to tissue located at and around the target. More specifically, CT images and CT image data sets acquired from CT scans are processed and assembled into a three-dimensional CT volume, which is then utilized to generate a three-dimensional model of patient P's airways. The three-dimensional model may be displayed on a display associated with computing device 122, or in any other suitable fashion. An example of such a user interface can be seen in FIG. 6. Using computing device 122, various views of the three-dimensional model or enhanced two-dimensional images generated from the three-dimensional model are presented. The enhanced two-dimensional images may possess some three-dimensional capabilities because they are generated from three-dimensional data. The three-dimensional model may be manipulated to facilitate identification of target on the three-dimensional model or two-dimensional images, and selection of a suitable pathway through patient P's airways to access tissue located at the target can be made. Once selected, the pathway plan, three-dimensional model, and images derived therefrom, can be saved and exported to a navigation system for use during the navigation phase(s).

As noted above a fluoroscopic imaging device 124 capable of acquiring fluoroscopic or x-ray images or video of the patient P (fluoroscopic image data sets) is also included in system 100. The images, sequence of images, or video captured by fluoroscopic imaging device 124 may be stored within fluoroscopic imaging device 124 or transmitted to computing device 122 for storage, processing, and display. Additionally, fluoroscopic imaging device 124 may move relative to the patient P so that images may be acquired from different angles or perspectives relative to patient P to create a sequence of fluoroscopic images, such as a fluoroscopic video. The pose of fluoroscopic imaging device 124 relative to patient P and while capturing the images may be estimated using the markers 121 and various pose estimation and image processing techniques. The markers 121 may be incorporated into the transmitter mat 120, incorporated into the operating table 112, or otherwise incorporated into another appliance placed on or near the operating table 112 so that they can be seen in the fluoroscopic images. The markers 121 are generally positioned under patient P and between patient P and a radiation source or a sensing unit of fluoroscopic imaging device 124. Fluoroscopic imaging device 124 may include a single imaging device or more than one imaging device.

Figure 2A:
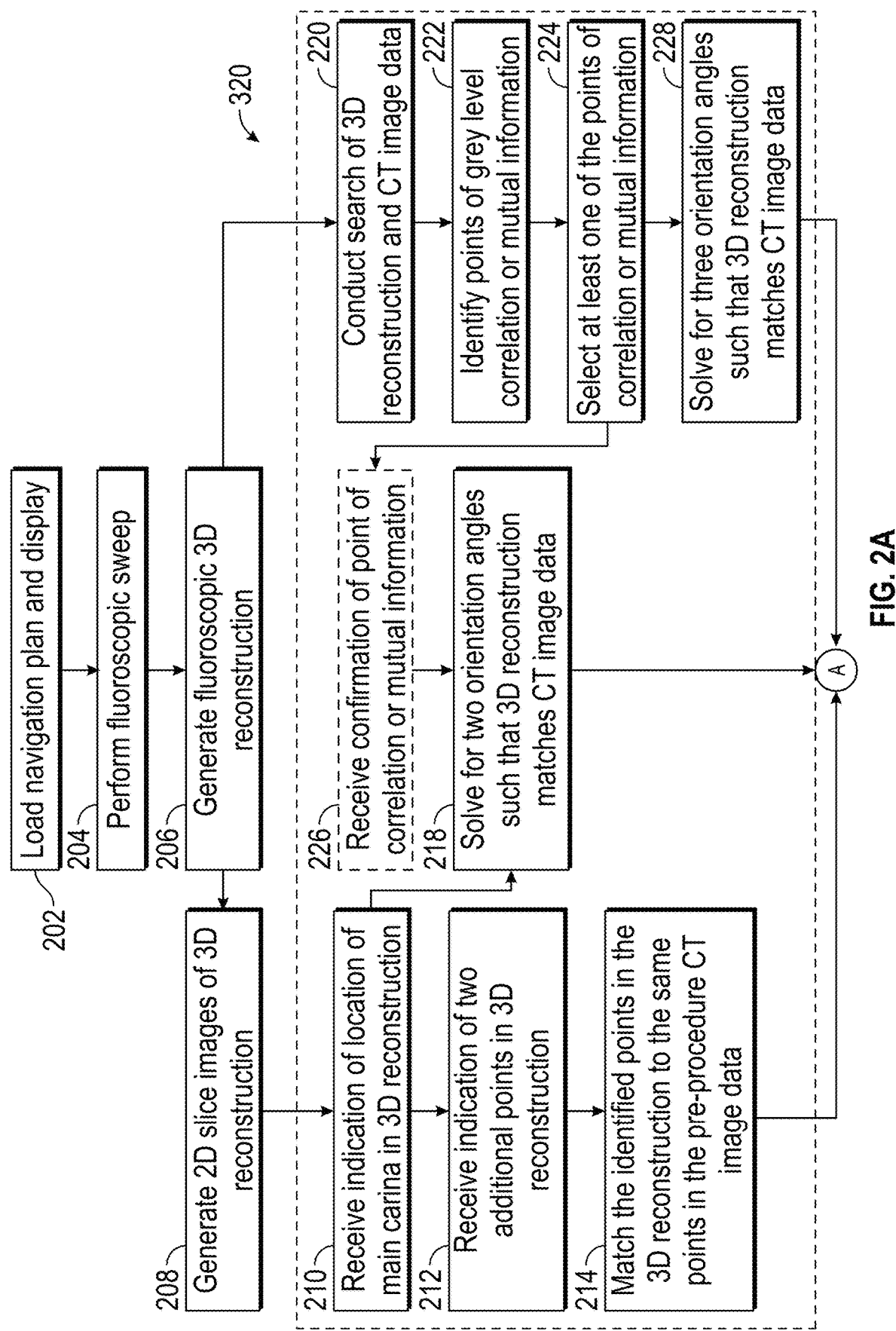
FIG. 2A is a partial flow chart of an imaging and navigation procedure in accordance with the disclosure.
Figure 2B:
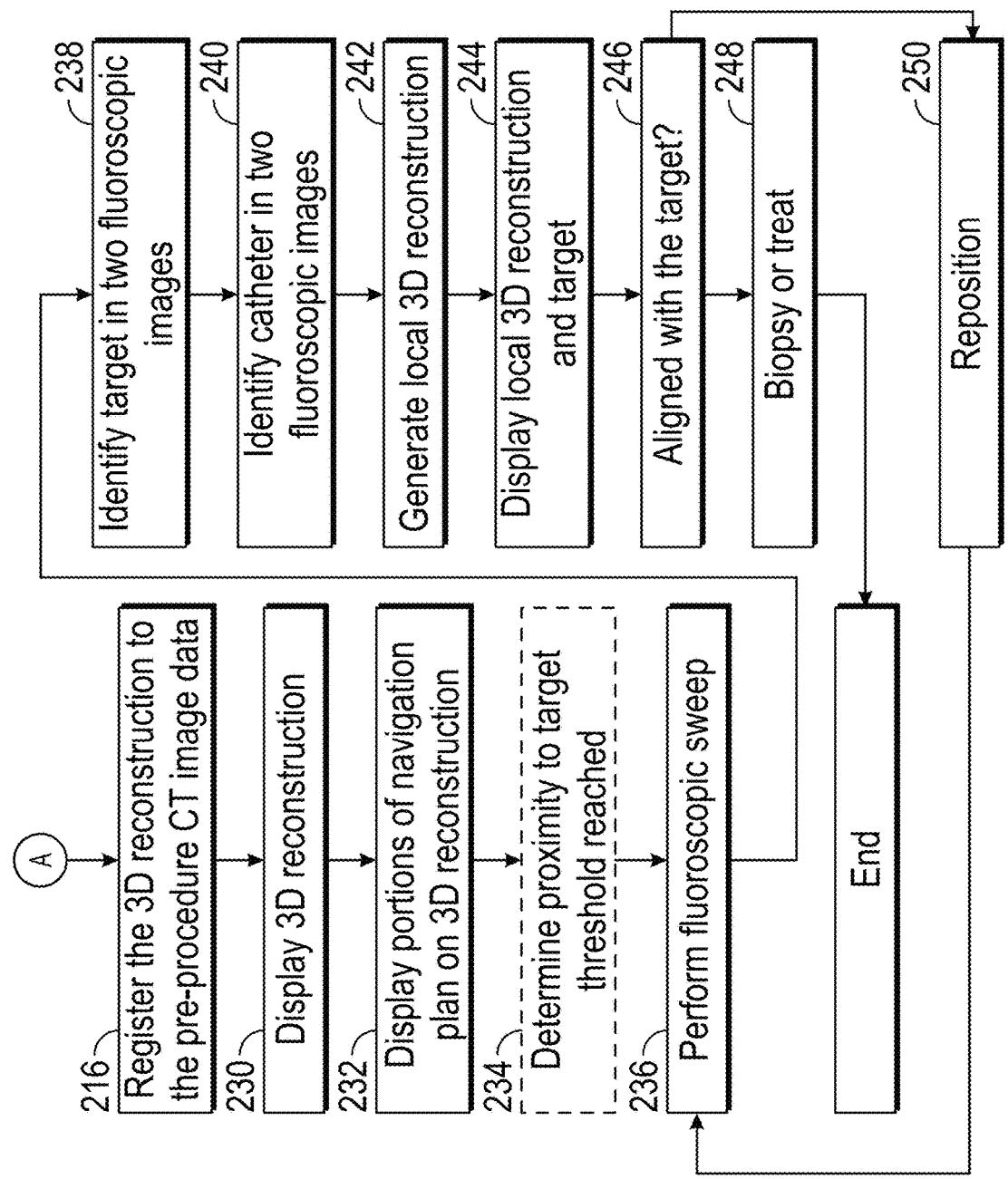
FIG. 2B is a partial flow chart of an imaging and navigation procedure in accordance with the disclosure.

One method 200 of employing the fluoroscopic imaging device 124 in system 100 is described with respect to FIGS. 2A and 2B. As an initial step 202, where a clinician wishes to review the navigation plan generated from the pre-procedure CT images, the navigation plan can be loaded and/or displayed on a display such as that associated with computer 122. After review of the navigation plan, the clinician may insert the one or more of the bronchoscope 108, catheter 106, LG 110 into the luminal network of the patient (e.g., the airways).

While the bronchoscope 108 captures images that can be viewed by the clinician as the bronchoscope 108 is advanced into the luminal network, the clinician cannot be confident that they are following the navigation plan derived from the pre-operative CT image data. In order to ensure that the bronchoscope 108 is following the navigation plan, a fluoroscopic sweep may be taken of the patient at step 204. That is, a series of fluoroscopic images may be acquired as the fluoroscopic imaging device 124 is rotated about the patient. This sweep may be between about 20 and 180 degrees about the patient, in some embodiments between 25 and 150 degrees, between 30 and 120 degrees, between 40 and 100 degrees, between 50 and 80 degrees, between 60 and 70 degrees and any whole number integer between these angle ranges. In particular embodiments, the sweep is 30, 40, or 50 degrees, though other angles of sweep may be undertaken without departure from the scope of the present disclosure.

Figure 4:
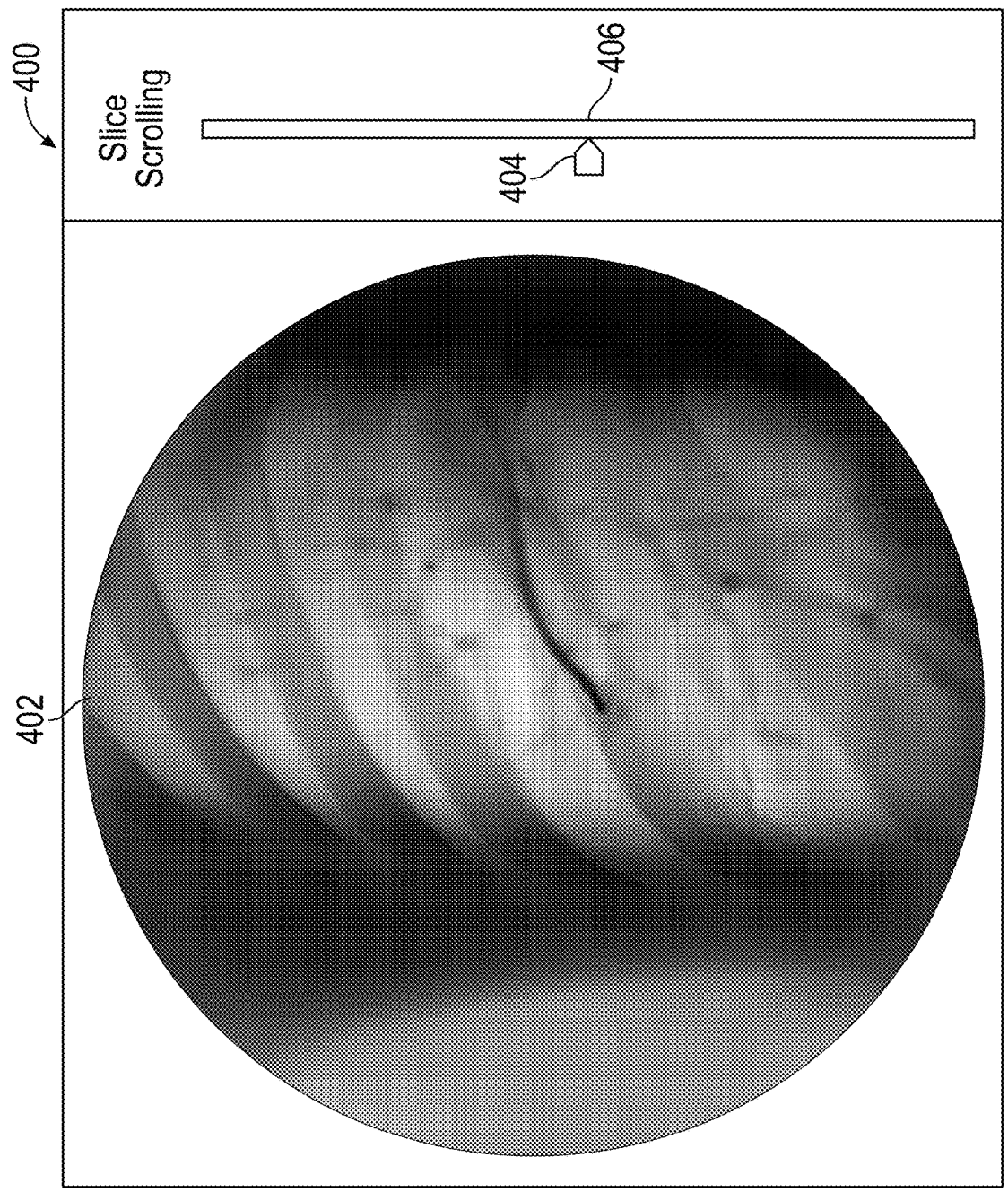
FIG. 4 depicts a user interface for marking structure in a fluoroscopic image in accordance with the disclosure.

Once a sufficient number of images are acquired, at step 206 a 3D reconstruction can be generated at step 206. The 3D reconstruction of the fluoroscopic images results in a 3D volume of the areas imaged during the fluoroscopic sweep. This 3D volume can be processed using a variety to techniques to provide real time information to the clinician. In a first technique, the 3D reconstruction can be processed to produce a series of 2D slice images at step 208. These 2D slice images are virtual fluoroscopic images in that they are generated from the 3D reconstruction but are ae not necessarily one of the fluoroscopic images acquired to render the 3D reconstruction. The 3D reconstruction may be sliced to produce 2D slice images along any axis a clinician might desire, but for orientation purposes the 2D images may be displayed in one or more of the standard axial, coronal or sagittal views. These slice images may be presented in a user interface in a way that a user can scroll through the slice images. FIG. 4 depicts a user interface 400 in which a user may scroll through a series of 2D slice images 402 using a tab 404 and bar 406 which represents the totality of the 2D slice images generated from the 3D reconstruction.

By scrolling through the 2D slice images an indication of the location of the main carina or another known anatomical feature may be identified by the clinician and the indication of the location of the main carina or another known anatomical feature can be received by the application at step 210. The main carina is a rigid cartilaginous tissue that is the first branching point of the airways in the lungs and marks the end of the trachea. In addition, the main carina is readily observable in fluoroscopic images and the 2D slice images from the fluoroscopic 3D reconstruction. However, other anatomical features are readily observable in fluoroscopic images and the 2D slice images from the fluoroscopic 3D reconstruction.

Depending on the application being executed by the processor in the computing device 122, the method may proceed to step 212, wherein the system 100 receives two more indications of points in the 3D reconstruction. These points may be carina, blood vessels, ribs, fissures, or other features in the 2D slices of the 3D reconstruction. The only limitation is that the point needs to be observable both in the 3D reconstruction and in the pre-procedure CT image data. As one example, the three points may be the main carina and the carina of the second bifurcation of the left and right lobes of the lungs. All three of these points should be readily visible in the 3D reconstruction, and specifically the 2D slice images of the 3D reconstruction. Similarly, these points should be readily visible in the pre-procedure CT image data and the 3D model generated therefrom. These points of registration may have been identified in the CT image data when constructing the 3D model and the navigation plan. Or these points may be identified after generation of the 3D reconstruction and the identification of the three points therein. In either event, the three points identified in both the 3D reconstruction and 3D model from the CT image data must be matched to one another at step 214.

This matching of three points in each of the 3D model and the 3D reconstruction allows for registration of the 3D model with the 3D reconstruction at step 216. Registration ensures that all features in the 3D model (not just the three points identified) are aligned with the 3D reconstruction.

As an alternative to receiving an indication of two addition points in the 3D reconstruction at step 212, the application may instead mathematically solve for the two additional degrees of freedom. That is, identification of the main carina or another known anatomical feature provides a single point for matching and secures a degree of freedom with respect to the comparison and registration of the 3D reconstruction and the 3D model from the CT image data. Specifically, by identifying the main carina or another known anatomical feature in the 3D reconstruction, the application has only a single point to register to the 3D model. However, with that single point secured, the 3D model need merely rotate the 3D reconstruction about three axes (e.g., X, Y, and Z), to seek to match the orientation of the 3D model to the 3D reconstruction along these axes. Thus, at step 218 the application solves for at least two orientation angels such that other points in the 3D reconstruction and the 3D model match. Again, the outcome of this matching is a registration of the pre-procedure 3D model and the 3D reconstruction at step 216. In accordance with one aspect of the disclosure the application solves for the two orientation angles by rotating the 3D reconstruction until it matches the 3D model as a comparison of the grey levels or brightness of certain features or other mutual information that appear in both the 3D model and the 3D reconstruction.

A third option for registration of the 3D reconstruction to the 3D model can be undertaken without receiving any indication of a point in the 3D reconstruction for matching to points in the 3D model (e.g., without even manually identifying the main carina). In accordance with this method, a search is conducted of the 3D reconstruction and the CT image data (or 3D model) at step 220. The search seeks out points of correlation between the 3D reconstruction and the CT image data by analyzing the grey levels and mutual information of the two image data sets. These points of grey level matching or mutual information are identified by the application at step 222. Once a sufficient number of the points are identified the application can select one or more of these points of correlation or mutual information. One of these points may well be the main carina, and the application can be optimized to solve for the main carina based on its size or general location or other parameters.

At step 224 the application can select at least one of these points of correlation or mutual information. Once selected there are two options, in one aspect at step 226, the application can present on a user interface a request for and receive a confirmation that the point of correlation or mutual information is correct. Once received this method proceeds to step 218 and solves for at least two orientation angels such that other points in the 3D reconstruction and the 3D model match, as described above.

Alternatively, rather than selecting just a single point at step 224 and receiving confirmation at step 226, multiple points may be selected by the application at step 224 and the application can proceed to step 228 where with multiple points of correlation and mutual information are identified the application can solve for all three orientation angles. Once these three angles are solved for the 3D reconstruction can be registered to the 3D model at step 316.

The process of the application selecting the points at step 224 and solving for the confirmation and mutual information at step 228 may be performed by computing device 122 storing in memory therein a learning algorithm. With each procedure, whether performed manually or automatically by the application, the results can be analyzed by the learning algorithm to refine the properties and parameters of a point to be selected in accordance with these methods. With each procedure the properties and parameters (e.g., brightness in in the CT images, proximity to other points, etc.) are identified and added to the empirical aspects of learning algorithm to further refine the algorithm for future procedures.

With respect to any of the processes described above, the computing device 122 may utilize the positions of the markers 121 in the fluoroscopic images. This technique relies on instances where the markers 121 are positioned in a non-repeating pattern. This non-repeating pattern, however, is known and the relative position of any single marker 121 to the antenna of the transmitter mat 120 are also known. Essentially the positions of the markers 121 as compared to the antennae of the transmitter mat 120 are registered to one another during manufacture of the transmitter mat 120. This known relative position of the marker 121 to the antennae of the transmitter mat 120 can be used by the computing device 122 and the fluoroscopic imaging device to identify specific ones of the markers 121 which appear in a fluoroscopic image. Once a marker 121 is identified in the fluoroscopic image, the computing device is able to register the coordinates of the fluoroscopic image to the coordinates of the antennae of the transmitter mat 121 using the known relative position of the marker 121 to the antennae of the transmitter mat 121. In this way, the position of a catheter in a 3D reconstruction can be compared to an EM detected position of the catheter, thus allowing the 3D reconstruction to be registered to the 3D model Once the 3D reconstruction and the 3D model from the navigation plan are registered to one another at step 216 the application may cause the 3D reconstruction to be displayed on a display associated with computing device 122 at step 230. With the display of the 3D reconstruction, now that the pre-procedure 3D model is registered with the 3D reconstruction, features from the navigation plan can be imported into and displayed on the 3D reconstruction. This may be as an overlay on the 3D reconstruction at step 232. Alternatively, the imported features from the 3D model can be fused with the 3D reconstruction. Other techniques for incorporating the features from the from the 3D model and the navigation plan with the 3D reconstruction may also be used without departing from the scope of the present disclosure. The features may be applied to the 3D reconstruction selectively. For example, the pathway plan may be shown in the 3D reconstruction, and/or an indication of the location of the target.

Once these features are imported into the displayed 3D reconstruction, the navigation plan can be followed until the catheter (e.g., bronchoscope 108, catheter 106) reaches the target. Optionally at step 234 the application can determine when, following the navigation plan the bronchoscope or tool is within a threshold distance from the target and provide an indication on a user interface. This may be done by comparing the bronchoscopic images generated by the bronchoscope to virtual bronchoscopic images generated from the 3D reconstruction. In instances where the bronchoscope has become wedged and no longer navigable through the airways, the proximity determination of the catheter 106 or other tools may require either a new fluoroscopic sweep (i.e. revert back to step 204), or other traditional fluoroscopic imaging techniques.

Figure 5:
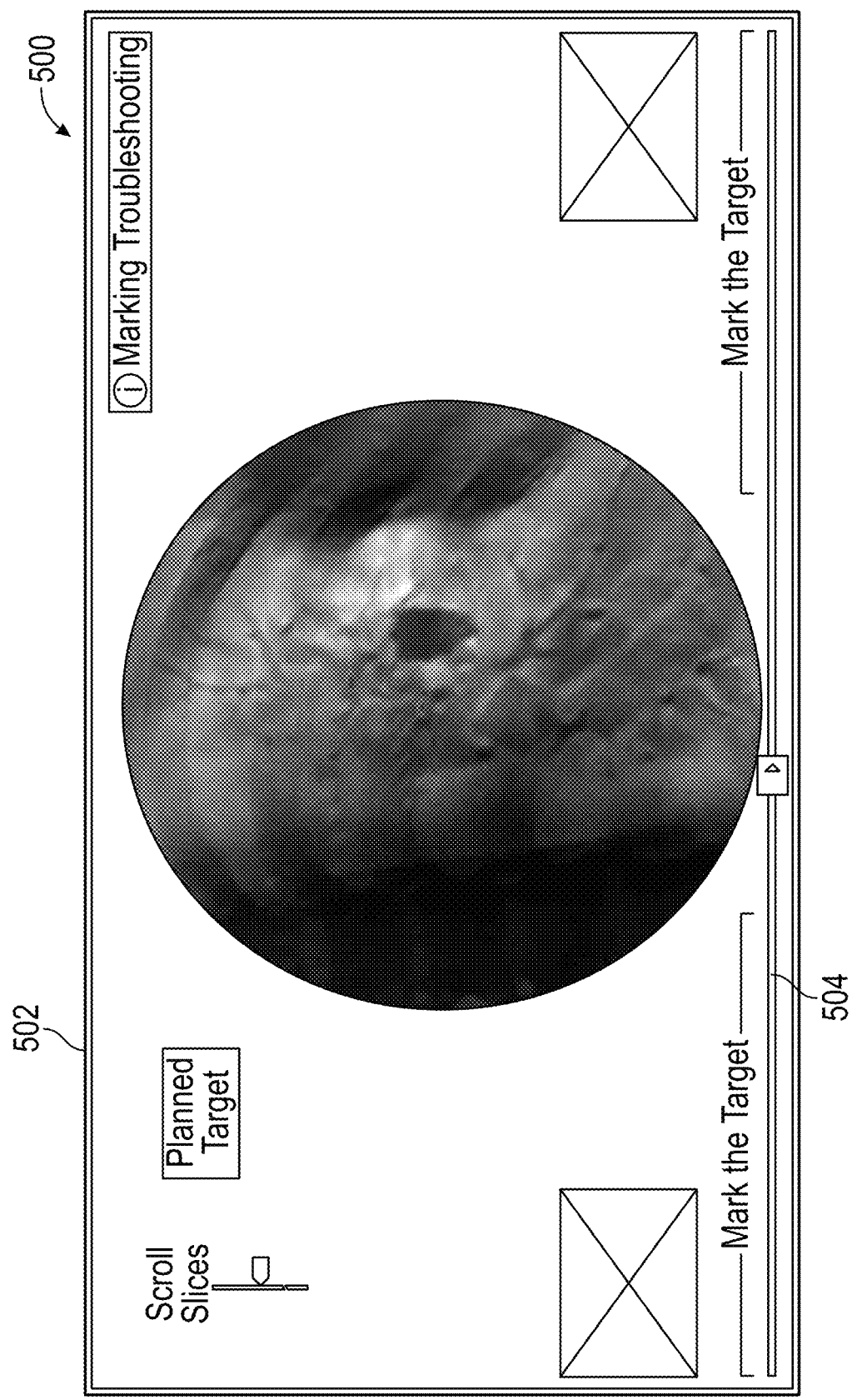
FIG. 5 depicts a user interface for marking a target in a fluoroscopic image in accordance with the disclosure.

Regardless, once the bronchoscope or tool is proximate the target, a second fluoroscopic sweep is undertaken at step 236. This second fluoroscopic sweep is to determine with heightened accuracy the location of the target and importantly the relative position of the bronchoscope or tool relative to the target. After the sweep is performed as described above, a user interface may present the user with a fluoroscopic image and request the user to identify the target in the fluoroscopic image at step 238. An example of a user interface 500 that may be presented to the user is shown in FIG. 5 in which scrollable fluoroscopic images 502 are presented to the user. Once identified in one fluoroscopic image 502, the user interface allows the user to scroll using a scroll bar 504 to identify a second fluoroscopic image in which to identify the target. Alternatively, the application may search the fluoroscopic images and automatically identify the target. Similarly, the user interface may present a user interface in which the user is identify the end of the catheter (e.g., bronchoscope 108 or catheter 106). This indication is received by the application at step 240.

Once the target and catheter are identified in the fluoroscopic images, a second 3D reconstruction can be generated at step 242 and displayed at step 244. This display of the 3D reconstruction includes a clear definition of the target marked in the fluoroscopic images of the fluoroscopic sweep at step 240. This provides an accurate indication of the location of the target, and the relative location of the catheter (e.g., bronchoscope 108 or catheter 106) and determinations can be made whether the catheter is aligned with the target, and the distance to the target from the end of the catheter. The relative position data may be displayed on the user interface or the clinician may simply make the determination of alignment based on observation of the 3D reconstruction. If the target and the bronchoscope or tool are aligned at step 246, the method may proceed to step 248 where a biopsy sample or a treatment is undertaken.

If it is determined that the tool and the target are not aligned the method proceeds to step 250 where the catheter (e.g., bronchoscope 108 or catheter 106) or tool is repositioned. After repositioning the method returns to step 236 to perform another fluoroscopic sweep. This procedure may be repeated as needed until alignment is achieved at step 246 and a biopsy or treatment can be undertaken at step 248.

As an alternative, the fluoroscopic sweep 236 can return the process back to the fluoroscopic sweep 204, where a new 3D reconstruction is generated at step 206. The process can then continue as described in steps 206-216, and all the permutations of registration (e.g., steps 210-228) described above, and the navigation plan data can be applied to and displayed in connection with the new 3D reconstruction.

Such quick generation of a 3D reconstruction of a region of interest can provide real-time 3D imaging of the target. Real-time imaging of the target and medical devices positioned in its area may benefit numerous interventional procedures, such as biopsy and ablation procedures in various organs, vascular interventions and orthopedic surgeries. For example, when navigational bronchoscopy is concerned, the aim may be to receive accurate information about the position of a catheter relative to the target to ensure accurate treatment or biopsy.

As another example, minimally invasive procedures, such as laparoscopy procedures, including robotic-assisted surgery, may employ intraoperative fluoroscopy to increase visualization, e.g., for guidance and lesion locating, and to prevent unnecessary injury and complications. Employing the above-mentioned systems and methods for real-time reconstruction of fluoroscopic 3D imaging of a target area and for navigation based on the reconstruction may benefit such procedures as well.

As noted above system 100 may be configured for electromagnetic navigation (EMN). When conducting EMN, the system 100 employs a six degrees-of-freedom electromagnetic locating or tracking system 114, or other suitable system for determining location data of a sensor 104 such as an EM sensor. Tracking system 114 is configured for use with a locatable guide 110 and particularly sensor 104. As described above, locatable guide 110 and sensor 104 are configured for insertion through catheter 106 into patient P's airways (either with or without bronchoscope 108) and are selectively lockable relative to one another via a locking mechanism.

Transmitter mat 120 is positioned beneath patient P. Transmitter mat 120 generates an electromagnetic field around at least a portion of the patient P within which the position of a plurality of reference sensors 118 and the sensor 104 can be determined with use of a tracking module 116. A second electromagnetic sensor 104 may also be incorporated into the end of the catheter 106. Additionally, or alternatively, the second electromagnetic sensor 104 may be incorporated into biopsy tools or treatment tools for use in the procedure.

The second electromagnetic sensor 104 may be a five degree-of-freedom sensor or a six degree-of-freedom sensor. One or more of reference sensors 118 are attached to the chest of the patient P. The six degrees of freedom coordinates of reference sensors 118 are sent to computing device 122 (which includes the appropriate software) where they are used to calculate a patient coordinate frame of reference.

When system 100 is configured for EMN, registration is needed to transform the detected EM coordinates of the sensor 104 to CT image data coordinates such that a detected location or position of the sensor can be displayed in the CT image data (e.g., in the 3D model or navigation plan) and updating of the detected position of the sensor 104 as it is navigated through the luminal network. As noted above, with EMN enabled systems 100, this registration can be undertaken (among other methods) by inserting the sensor 104 into the airways and generating a point cloud of detected positions of the sensor 104. Matching of the point cloud to the airways of the 3D model registers the patient's actual airways to the 3D model. In addition, this process defines a translation from the EMN coordinates (where the sensor is detected in the EM field) to the CT image data coordinates. In this manner, the navigation plan can be followed and the detected location of the sensor 104 can be presented in the 3D model as the sensor 104, and therewith the catheter (e.g., bronchoscope 108 or catheter 106) is traversed through the luminal network.

However, when using the fluoroscopic imaging techniques described above to perform the initial registration of a navigation plan to a patient's luminal network, there is no bridge from the EM coordinates to the CT image data coordinates, and thus no way to update progress in the navigation plan as the catheter is navigated through the luminal network. While repeated fluoroscopic imaging is possible to update the position of the catheter (e.g., bronchoscope 108 or catheter 106) in the navigation plan, this results in additional radiation to the patient and the clinical staff. Instead, the bridge between EM coordinates and CT coordinates can be achieved by using fluoroscopic imaging techniques. Specifically, a registration of the fluoroscopic image data from the fluoroscopic sweep with the detected position of the sensor 104 in combination with a registration of the fluoroscopic image data with the pre-operative CT image data and navigation plan, results in an empirical transform that allows for registration of the EM coordinate system with the pre-operative CT image data coordinate system.

Figure 3A:
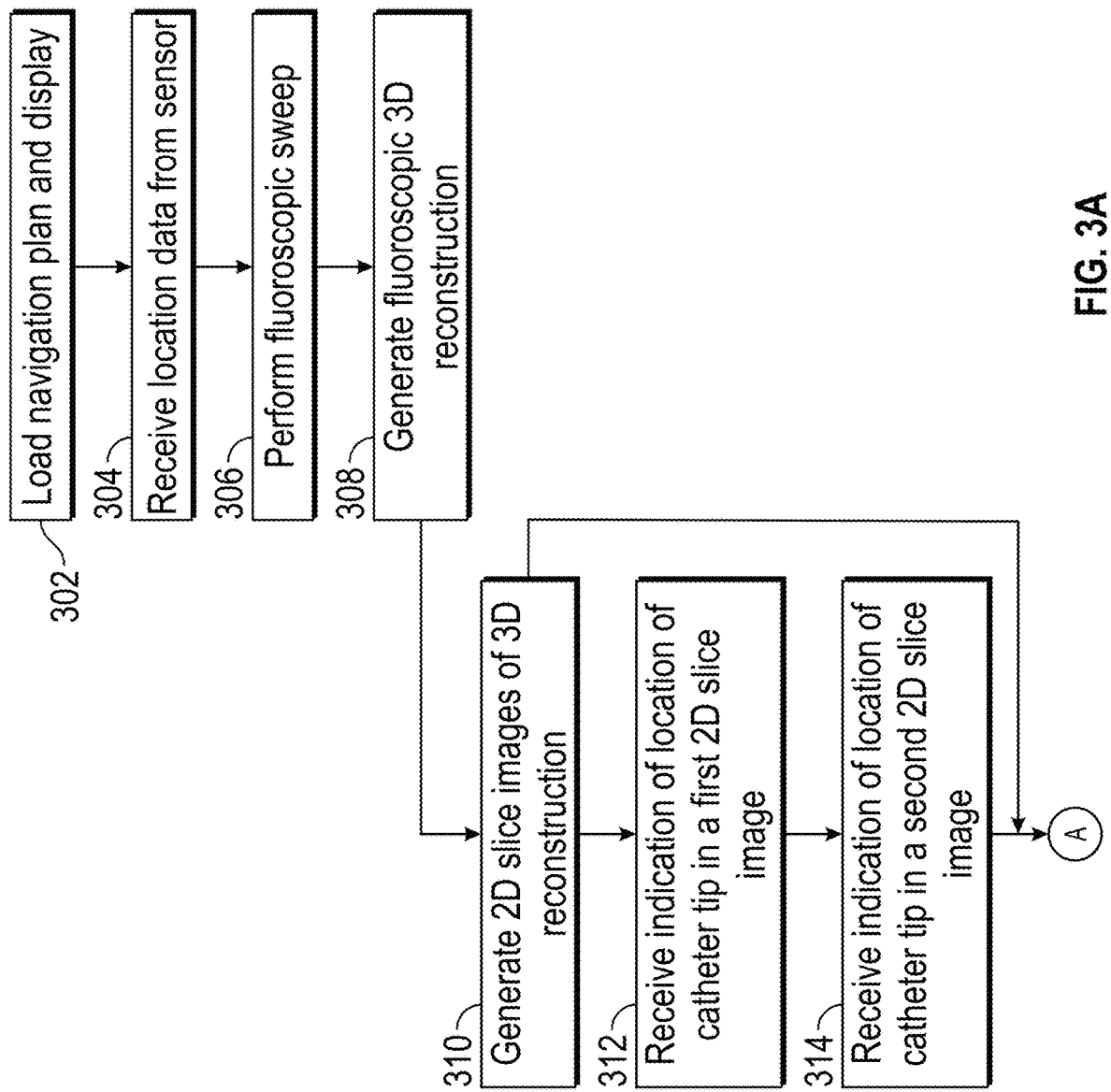
FIG. 3A is a partial flow chart of an imaging and navigation procedure in accordance with the disclosure.
Figure 3B:
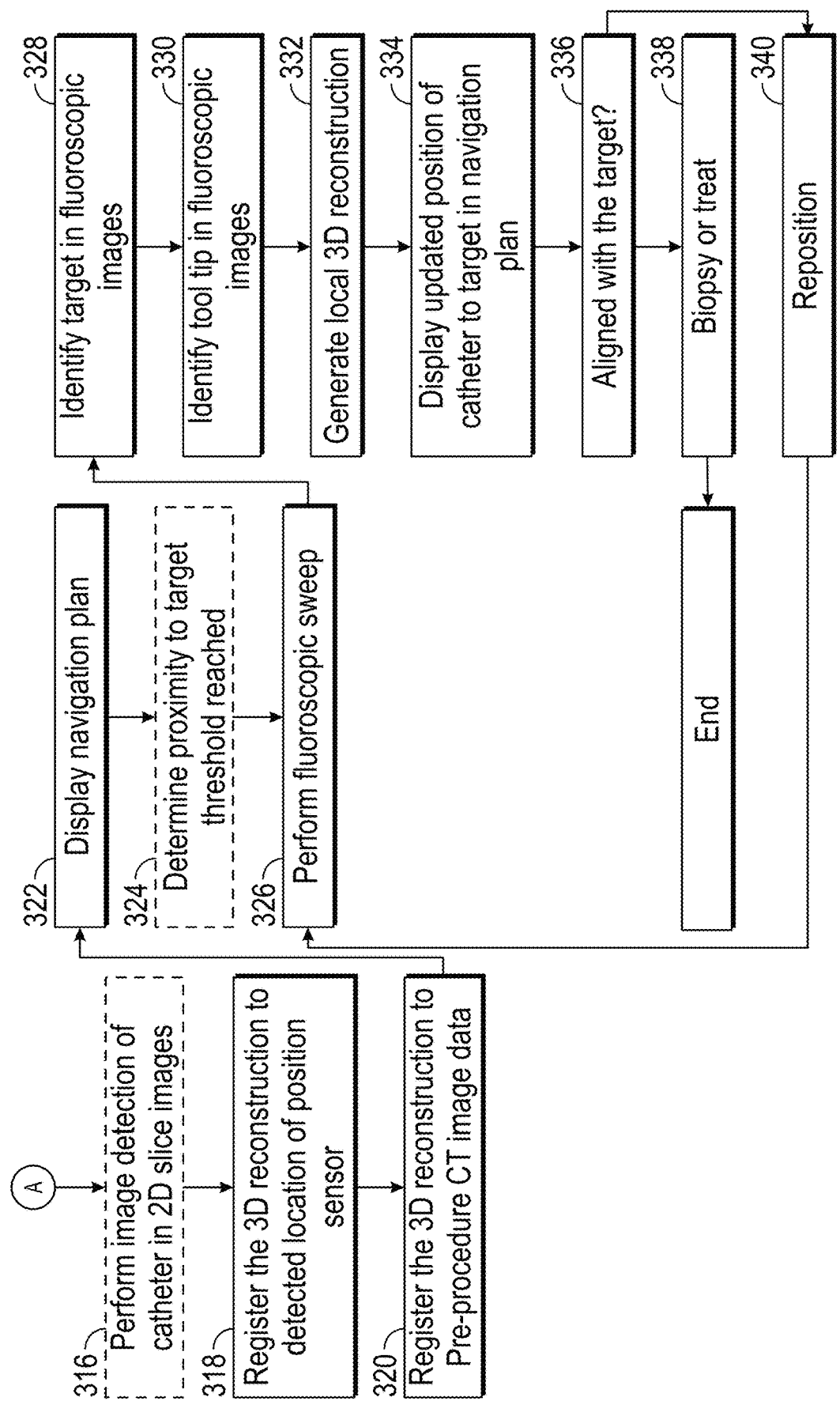
FIG. 3B is a partial flow chart of an imaging and navigation procedure in accordance with the disclosure.

FIGS. 3A and 3B depict a method of performing registration of the fluoroscopic image data to the detected EMN coordinates of a sensor 104. Method 300 starts with an application on computing device 122 loading the navigation plan developed from the pre-procedure CT image data at step 302. Once loaded, a catheter (e.g., bronchoscope 108 or catheter 106) including a sensor 104 may be inserted into the EM field generated by the transmitter mat 120. As shown in FIG. 1 the transmitter mat 120 is placed directly beneath the patient P and the EM field will be generated around the patient. In the scenario where lung navigation is desired, placement of the sensor 104 in the EM field will include placement of a catheter (e.g., bronchoscope 108 or catheter 106) having the sensor 104 into the airways of the patient, for example to a point near the main carina. The exact location of placement of the catheter and sensor 104 is not critical so long as is at a location that can be imaged by the fluoroscopic imaging device 124. Once within the EM field the sensor 104 will generate an electrical current that can be analyzed by the locating module 116 in the tracking system 114 to determine the position of the sensor 104 in the EM field at step 304. That is step 304 identifies the EM coordinates (location data) of the sensor 104.

At this point the fluoroscopic imaging device 124 can undertake a fluoroscopic sweep at step 306. A 3D reconstruction may be formed from the images taken by the fluoroscopic imaging device 124 at step 308, and 2D slice images of the 3D reconstruction are generated at step 310. Steps 306-310 may be the same steps as 204-208 of FIG. 2A and need not be repeated.

Figure 4A:
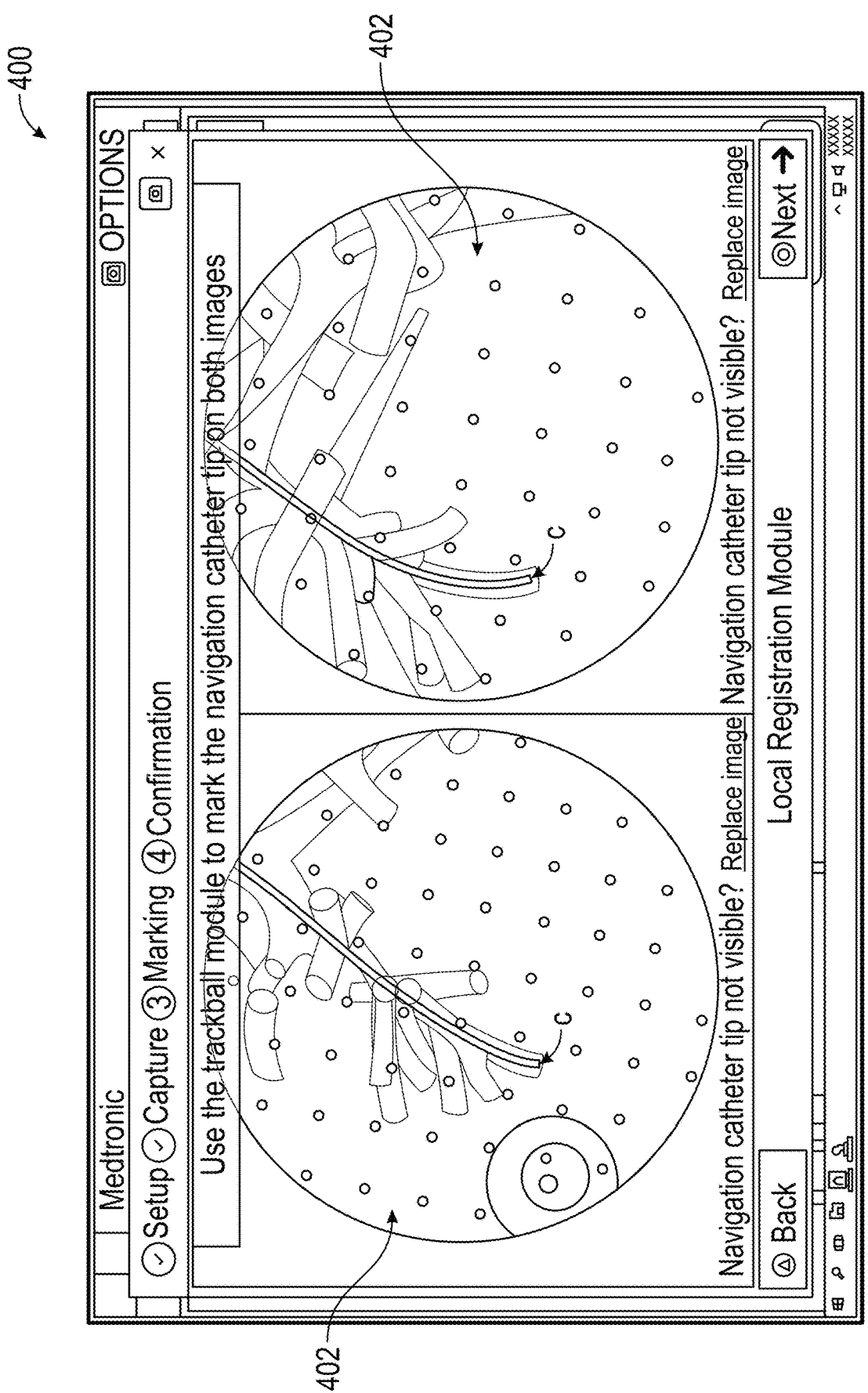
FIG. 4A depicts a user interface for marking a catheter in a fluoroscopic image in accordance with the disclosure.

Once the 2D slice images are generated, the application may at step 312 present one of the slices to the user on a user interface and request the user identify the location of a catheter tip in the image as depicted in FIG. 4 or 4A. The location of the distal tip of the catheter (e.g., the bronchoscope 108, the catheter 106, the LG 110, or a biopsy or treatment tool) serves as an identification of the location of the sensor 104 in the 2D slice images. The location of the sensor 104 relative to the tip of the catheter may be known to the application, for example saved in the memory of computing device 122. At step 314, the user interface presents a second 2D slice image from the 3D reconstruction and requests identification of the tip of the catheter in the second 2D slice image. As shown in FIG. 4A these two images may be presented simultaneously. If the two images are from wide-spread portions of the fluoroscopic sweep (i.e. at wide angles from one another), the application can accurately determine the position catheter tip, and there with the location of the sensor 104 in the 3D reconstruction.

Because the location of the sensor 104 in the EM field is known from the locating module 116 and has been determined in the 3D reconstruction, the EMN coordinate systems and the coordinate system of the fluoroscopic imaging device 124 can be registered to one another at step 318.

Instead of receiving an indication of the location of the catheter tip in two 2D slice images, the application may perform an image processing step of identifying the catheter at step 316. This may optionally be assisted by the presence of fiducial markers formed along the length of the catheter at intervals. Even without the fiducial markers, the shape of the catheter (e.g., the bronchoscope 108, catheter 106, LG 110, or biopsy or treatment tools) should be readily identifiable in the 2D slices of the fluoroscopic 3D reconstruction. By identifying the catheter in each of the 2D slice images, the application can determine location of the tip and therewith the location of the sensor 104 in the 3D reconstruction.

In addition to either the receipt of the manual identification of the location of the catheter tip or the automated image processing process, a combination of the two is also contemplated by the instant application. In such a scenario, the application receives an indication of the location of the catheter tip in two images and conducts image processing for all or a substantial portion of the of the remaining 2D slice images. Following this combined process, the transform of the coordinates of the fluoroscopic imaging device 124 and image data derived therefrom to the EMN coordinates is derived and the 3D reconstruction and be registered to the detected position of the sensor 104, 128 in the EM field.

At step 320 the registration of 3D reconstruction to the pre-procedure CT image data can be undertaken, as described above. Any of the methods for registering the 3D reconstruction with the pre-procedure CT image data may be employed. Once both registration processes have been undertaken, all three coordinate systems are registered to one another. Fluoroscopic coordinate system to the pre-procedure CT imaging coordinate system and Fluoroscopic coordinate system to EMN coordinate system. As a result, a transform is established for registration of EMN coordinates to the pre-procedure CT imaging coordinate system.

By way of the multiple registrations the application can proceed either by simply using the registration of the sensor 104 with the pre-procedure CT image data to update the detected position of the EM sensor in the navigation plan developed from the pre-procedure CT image data and display the navigation plan at step 322. Using the navigation plan, the detected position of the sensor 104, and following a pathway defined in the navigation plan the sensor 104 can be navigated to a target in the navigation plan.

Optionally at step 324 the application can determine when, following the navigation plan the catheter (e.g., bronchoscope 108 or WC 1060 is within a threshold distance from the target and provide an indication on a user interface. Regardless, once the catheter is proximate the target, a second fluoroscopic sweep is undertaken at step 326. This second fluoroscopic sweep is to determine with heightened accuracy the location of the target and importantly the relative position of the bronchoscope 108 or another tool relative to the target. After the sweep is performed as described above, a user interface may present the user with a fluoroscopic image and request the user to identify the target in the fluoroscopic image, the identity of the target is received by the application at step 328. Once identified, the user interface may present the user with a second fluoroscopic image in which to identify the target as shown in FIG. 5. Alternatively, the application may search the fluoroscopic images and automatically identify the target.

Figure 6:
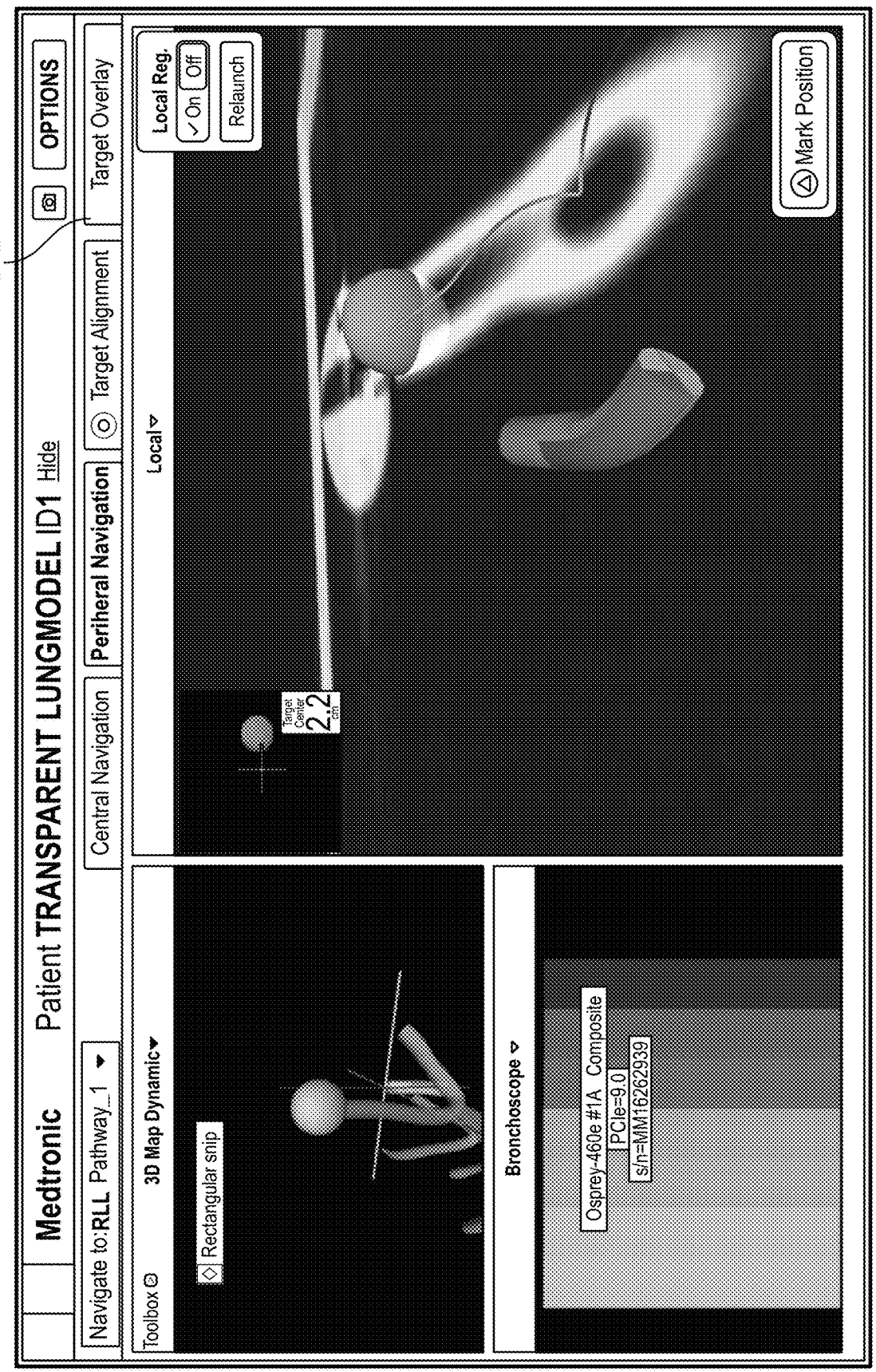
FIG. 6 depicts a user interface for navigation to a target in accordance with the disclosure.

Once the target is identified in the fluoroscopic images, the user interface may present the user with fluoroscopic images in which identify the catheter tip in the fluoroscopic images, the identity of the catheter tip is received by the application at step 330 as shown in FIGS. 4 and 4A. A second 3D reconstruction can be generated at step 332 and the relative position of the catheter tip and the target can be updated in the navigation plan derived from the pre-procedure CT image data. This updated relative position can be displayed on the user interface 602 in the navigation plan at step 334 as seen in FIG. 6. This provides an accurate indication of the location of the catheter tip with respect to the target, and determinations can be made whether the sensor 104 is aligned with the target, and the distance to the target from the sensor 104 and therewith from the end of the bronchoscope 108 or other tool. This data may be displayed on the user interface or the clinician may simply make the determination of alignment based on observation of the 3D reconstruction. If the target and the bronchoscope or tool are aligned at step 336, the method may proceed to step 338 where a biopsy sample or a treatment is undertaken.

If it is determined that the sensor 104 and the target are not aligned the method proceeds to step 340 where the bronchoscope 108 or another tool is repositioned. After repositioning the method returns to step 326 to perform another fluoroscopic sweep. This procedure may be repeated as needed until alignment is achieved at step 338 and a biopsy or treatment can be undertaken at step 338.

Figure 8:
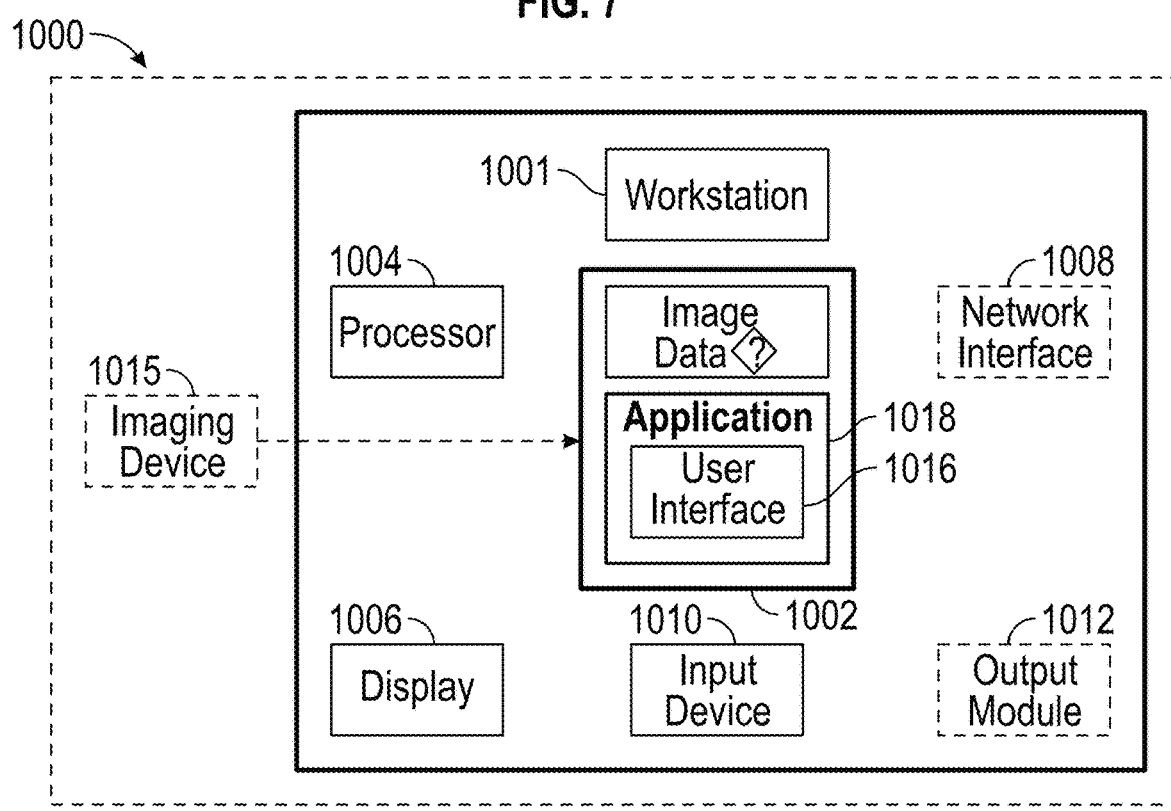
FIG. 8 depicts features and components of a computing device in accordance with the disclosure.

Reference is now made to FIG. 8, which is a schematic diagram of a system 1000 configured for use with the methods of the disclosure including the methods of FIGS. 2 and 3. System 1000 may include a workstation 1001, and optionally a fluoroscopic imaging device or fluoroscope 1015. In some embodiments, workstation 1001 may be coupled with fluoroscope 1015, directly or indirectly, e.g., by wireless communication. Workstation 1001 may include a memory 1002, a processor 1004, a display 1006 and an input device 1010. Processor or hardware processor 1004 may include one or more hardware processors. Workstation 1001 may optionally include an output module 1012 and a network interface 1008. Memory 1002 may store an application 1018 and image data 1014. Application 1018 may include instructions executable by processor 1004 for executing the methods of the disclosure including the method of FIGS. 2 and 3.

Application 1018 may further include a user interface 1016. Image data 1014 may include the CT scans, the generated fluoroscopic 3D reconstructions of the target area and/or any other fluoroscopic image data and/or the generated one or more virtual fluoroscopy images. Processor 1004 may be coupled with memory 1002, display 1006, input device 1010, output module 1012, network interface 1008 and fluoroscope 1015. Workstation 1001 may be a stationary computing device, such as a personal computer, or a portable computing device such as a tablet computer. Workstation 1001 may embed a plurality of computer devices.

Memory 1002 may include any non-transitory computer-readable storage media for storing data and/or software including instructions that are executable by processor 1004 and which control the operation of workstation 1001 and, in some embodiments, may also control the operation of fluoroscope 1015. Fluoroscope 1015 may be used to capture a sequence of fluoroscopic images based on which the fluoroscopic 3D reconstruction is generated and to capture a live 2D fluoroscopic view according to this disclosure. In an embodiment, memory 1002 may include one or more storage devices such as solid-state storage devices, e.g., flash memory chips. Alternatively, or in addition to the one or more solid-state storage devices, memory 1002 may include one or more mass storage devices connected to the processor 1004 through a mass storage controller (not shown) and a communications bus (not shown).

Although the description of computer-readable media contained herein refers to solid-state storage, it should be appreciated by those skilled in the art that computer-readable storage media can be any available media that can be accessed by the processor 1004. That is, computer readable storage media may include non-transitory, volatile and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid-state memory technology, CD-ROM, DVD, Blu-Ray or other optical storage, magnetic cassettes, magnetic tape, magnetic disk storage or other magnetic storage devices, or any other medium which may be used to store the desired information, and which may be accessed by workstation 1001.

Application 1018 may, when executed by processor 1004, cause display 1006 to present user interface 1016. User interface 1016 may be configured to present to the user a single screen including a three-dimensional (3D) view of a 3D model of a target from the perspective of a tip of a medical device, a live two-dimensional (2D) fluoroscopic view showing the medical device, and a target mark, which corresponds to the 3D model of the target, overlaid on the live 2D fluoroscopic view. User interface 1016 may be further configured to display the target mark in different colors depending on whether the medical device tip is aligned with the target in three dimensions.

Network interface 1008 may be configured to connect to a network such as a local area network (LAN) consisting of a wired network and/or a wireless network, a wide area network (WAN), a wireless mobile network, a Bluetooth network, and/or the Internet. Network interface 1008 may be used to connect between workstation 1001 and fluoroscope 1015. Network interface 1008 may be also used to receive image data 1014. Input device 1010 may be any device by which a user may interact with workstation 1001, such as, for example, a mouse, keyboard, foot pedal, touch screen, and/or voice interface. Output module 1012 may include any connectivity port or bus, such as, for example, parallel ports, serial ports, universal serial busses (USB), or any other similar connectivity port known to those skilled in the art.

While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular aspects.

What is claimed is:

1. A method of registering two image data sets, comprising:
    performing a fluoroscopic sweep of a desired portion of a patient to generate a fluoroscopic image data set;
    generating a three-dimensional (3D) reconstruction from data received from the fluoroscopic sweep;
    generating a two-dimensional (2D) slice images from the 3D reconstruction, wherein the 2D slice images are virtual fluoroscopic images;
    presenting the 2D slice images on a user interface to enable scrolling of the 2D images of the 3D reconstruction;
    conducting a search of the 3D reconstruction and pre-procedure CT image data to identify at least one point of grey level correlation or mutual information;
    registering the 3D reconstruction to the pre-procedure CT image data wherein the registering includes solving for two angles of orientation by rotating the 3D reconstruction about three axes such that the 3D reconstruction matches the CT image data along the three axes;
    displaying the 3D reconstruction; and
    displaying portions of a navigation plan associated with the pre-procedure CT image data on the 3D reconstruction based on the registration.

2. The method of claim 1, wherein the 3D reconstruction matches a 3D model derived from the pre-procedure CT image data.

3. The method of claim 1, wherein displaying portions of a navigation plan depicts a position of a target identified in the pre-procedure CT image data on the 3D reconstruction.

4. The method of claim 3, wherein displaying portions of a navigation plan depicts a pathway through a luminal network to the target.

5. The method of claim 1, further comprising performing a second fluoroscopic sweep.

6. The method of claim 5, further comprising identifying a target in two fluoroscopic images from the second fluoroscopic sweep.

7. The method of claim 6, further comprising identifying a portion of a catheter in two fluoroscopic images from the second fluoroscopic sweep.

8. The method of claim 7, further comprising generating a local 3D reconstruction.

9. The method of claim 8, further comprising confirming that the catheter is aligned with the target in the 3D reconstruction; and
    performing a medical procedure on the target.

10. A system for registering fluoroscopic image data with pre-operative CT image data comprising:
    a computing device including a processor and a memory, the memory storing therein an application that when executed by the processor causes the processor to execute the steps of:
        generating a three-dimensional (3D) reconstruction from data received from a fluoroscopic sweep;
        generating a two-dimensional (2D) slice images from the 3D reconstruction, wherein the 2D slice images are virtual fluoroscopic images;
        presenting the 2D slice images on a user interface to enable scrolling of the 2D images of the 3D reconstruction;
        conducting a search of the 3D reconstruction and pre-procedure CT image data to identify at least one point of grey level correlation or mutual information;
        selecting at least one point of grey level correlation or mutual information;
        registering the 3D reconstruction to the pre-procedure CT image data wherein the registering includes solving for two angles of orientation by rotating the 3D reconstruction about three axes such that the 3D reconstruction matches the CT image data along the three axes; and
    a display for displaying portions of a navigation plan associated with the pre-procedure CT image data on the 3D reconstruction based on the registering.

11. The system of claim 10, wherein the application when executed further causes the processor to perform a step of performing a second fluoroscopic sweep.

12. The system of claim 11, wherein the application when executed further causes the processor to perform a step of identifying a target in two fluoroscopic images from the second fluoroscopic sweep.

13. The system of claim 12, wherein the application when executed further causes the processor to perform a step of identifying a portion of a catheter in two fluoroscopic images from the second fluoroscopic sweep.

14. The system of claim 13, wherein the application when executed further causes the processor to perform a step of generating a local 3D reconstruction.

15. The system of claim 14, wherein the application when executed further causes the processor to perform steps of:
confirming that the catheter is aligned with the target in the 3D reconstruction; and
performing a medical procedure on the target.

* * * * *